United States Patent [19]
Wolvek et al.

[11] Patent Number: 5,911,707
[45] Date of Patent: Jun. 15, 1999

[54] NEEDLE GUIDE

[75] Inventors: Sidney Wolvek, Brooklyn; Debra L. Joseph, Wallkill, both of N.Y.; Kenneth L. Waters, Lawrenceville, N.J.

[73] Assignee: Datascope Investment Corp., Montvale, N.J.

[21] Appl. No.: 08/838,712

[22] Filed: Apr. 9, 1997

[51] Int. Cl.[6] .................................................. A61M 5/00
[52] U.S. Cl. ........................ 604/116; 604/174; 604/180; 128/DIG. 26
[58] Field of Search ..................... 604/116, 117, 604/174, 177, 180; 128/DIG. 26

[56] References Cited

U.S. PATENT DOCUMENTS

| | | | |
|---|---|---|---|
| 2,198,666 | 4/1940 | Gruskin | 604/117 |
| 2,402,306 | 6/1946 | Turkel | 604/174 |
| 3,167,072 | 1/1965 | Stone et al. | 604/116 X |
| 4,314,568 | 2/1982 | Loving | 604/116 X |
| 4,332,248 | 6/1982 | De Vitis | 604/117 X |
| 4,571,243 | 2/1986 | Froning et al. | |
| 4,820,282 | 4/1989 | Hogan | 604/177 X |
| 4,878,897 | 11/1989 | Katzin | 128/DIG. 26 |
| 4,883,053 | 11/1989 | Simon | 604/116 X |
| 4,966,589 | 10/1990 | Kaufman | 604/116 X |
| 5,053,042 | 10/1991 | Bidwell | |
| 5,100,387 | 3/1992 | Ng | |
| 5,235,987 | 8/1993 | Wolfe | |
| 5,292,325 | 3/1994 | Gurmarnik | 128/DIG. 26 |
| 5,437,640 | 8/1995 | Schwab | |
| 5,499,630 | 3/1996 | Hiki et al. | |

FOREIGN PATENT DOCUMENTS 126984  12/1949  Sweden.

*Primary Examiner*—Corrine McDermott
*Assistant Examiner*—LoAn H. Thanh
*Attorney, Agent, or Firm*—Lerner, David, Littenberg, Krumholz & Mentlik, LLP

[57] ABSTRACT

A needle guide ensures that an angiographic needle is inserted into a patient's femoral artery at a prescribed location, angle and direction. The needle guide includes an elongated base having a recess on one end defined by a pair of projecting fingers, and a support member on the upper surface of the base adjacent to the recess. The support member has a support surface which is inclined at a prescribed angle with respect to a locating plane defined by the base. The length of the projecting fingers help position the support surface at a spaced distance from the patient's inguinal crease, while a channel in the support surface cradles and guides the angiographic needle at the prescribed angle as it is inserted into the femoral artery. The needle guide may include a second recess defined by a pair of projecting fingers at the opposite end of the base and another support member adjacent thereto. This other support member may have a support surface inclined at an angle relative to the locating plane of the base which is different from the angle the first support member makes with the locating plane of the base. Thus, depending upon the direction in which it is oriented, the needle guide may be used to insert a needle at one of two different angles.

20 Claims, 3 Drawing Sheets

NEEDLE GUIDE

FIELD OF THE INVENTION

The present invention relates generally to catheterization procedures and, more particularly, to the insertion of an angiographic needle into a patient's artery to commence such procedures. Still more particularly, the present invention is directed to a device for guiding the insertion of an angiographic needle into the patient's femoral artery at a prescribed angle and direction.

BACKGROUND OF THE INVENTION

Numerous medical procedures involve percutaneous insertions into a vein or artery. Among the more common are cardiac catheterization, intra-aortic balloon pumping (IABP) and percutaneous transluminal coronary angioplasty (PTCA). Each of these procedures typically begins with the placement of an angiographic needle through the skin and tissue of the patient's leg at a pulse point of the femoral artery immediately below the inguinal or groin crease. The needle is introduced until a spurt of arterial blood exits the needle hub, indicating that the tip of the needle has entered the femoral artery. A guidewire is then inserted through the needle and up through the femoral and iliac arteries into the aorta. The needle may then be removed, leaving the guidewire in place to serve as a guide for the insertion of an introducer sheath assembly or for the insertion of the intra-aortic balloon itself in the case of sheathless percutaneous procedures.

In order to ensure proper guidewire insertion, it is important that the angiographic needle enter the femoral artery at as shallow an angle as possible. Angles which are too shallow for a particular patient, however, may increase the distance between the artery and the patient's skin such that the needle is unable to reach and penetrate the artery, or may cause the needle to slide across the outside surface of the artery without entering it squarely. On the other hand, angles that are too steep may force the guidewire to make a sharp bend as it enters the artery. This sharp bend may create a kink in the guidewire, making it useless as a guide for the subsequent insertion of other devices. Hence, insertion of the needle at either too steep or too shallow an angle is unacceptable, and will require that the procedure be repeated in the contralateral leg. For patients of average weight, an entry angle of about 30° is desirable. However, when a patient is obese, entry at an angle of about 30° creates difficulties because of the extra thickness of the tissue overlying the artery. Therefore, obese patients often require entry at a more steep angle, with an entry angle of about 45° being particularly desirable.

In addition to the importance of the angle at which the needle is inserted into the artery is the angle at which the needle is inserted relative to the axis of the patient's leg. If this angle is not correct, the needle may nick the artery rather than enter it squarely, again requiring that the procedure be repeated in the opposite leg.

As a result of these limitations on the orientation of the needle as it enters the femoral artery, positioning and orienting the needle by eye often results in insertion difficulties. There therefore exists a need for a device which will assure the insertion of an angiographic needle at the proper angle relative to the femoral artery and in the proper direction relative to the axis of the patient's leg so as to enable guidewires to be inserted into the artery without difficulty. Preferably, such a device will be inexpensive to manufacture so as to be disposable, and will accommodate needle insertions in patients of average weight, as well as in patients who are obese.

SUMMARY OF THE INVENTION

The present invention addresses these needs. One embodiment of the present invention provides a needle guide including a base having a length extending in an axial direction and a surface defining an orientation plane. The base preferably has a dimension in the axial direction which is greater than its dimension in a direction perpendicular to the axial direction. A first support member on the base defines a needle guide path orientation inclined at a first angle relative to the orientation plane, and a second support member on the base has defines a needle guide path inclined at a second angle relative to the orientation plane, the second angle being different from the first angle. The first angle preferably is between about 20° and about 40°, and most preferably is about 30°. The second angle preferably is between about 40° and about 60°, and most preferably is about 45°.

In preferred embodiments, the needle guide paths of the first and second support members include a channel for slidably receiving a needle. Preferably, these channels extend in alignment with the axial direction of the base. The needle guide also may include locators for locating the first and second support members at at least preselected spaced distances from the inguinal crease of the patient, the preselected spaced distances being related to the inclination angle of the needle guide path.

In another embodiment of the present invention, the needle guide includes a base having a length extending in an axial direction between a first end and a second end and a surface defining an orientation plane. A pair of fingers project from the first end of the base in the axial direction and are spaced apart from one another to define a recess therebetween. A first support member on the base defines a needle guide path inclined at a first angle relative to the orientation plane so that an edge of the needle guide path which is closest to the first end of the base is lower than an edge of the needle guide path which is farthest from the first end of the base.

In one variant of this embodiment, the first angle is between about 20° and about 40°, and preferably is about 30°. In another variant hereof, the first angle is between about 40° and about 60°, and preferably is about 45°.

In preferred embodiments, the needle guide further includes a channel in the needle guide path of the support member for slidably receiving the needle. The channel desirably extends in alignment with the axial direction.

BRIEF DESCRIPTION OF THE DRAWINGS

A more complete appreciation of the subject matter of the present invention and the various advantages thereof can be realized by reference to the following detailed description, in which reference is made to the accompanying drawings in which.

DETAILED DESCRIPTION OF THE PREFERRED EMBODIMENTS

Figure 1:
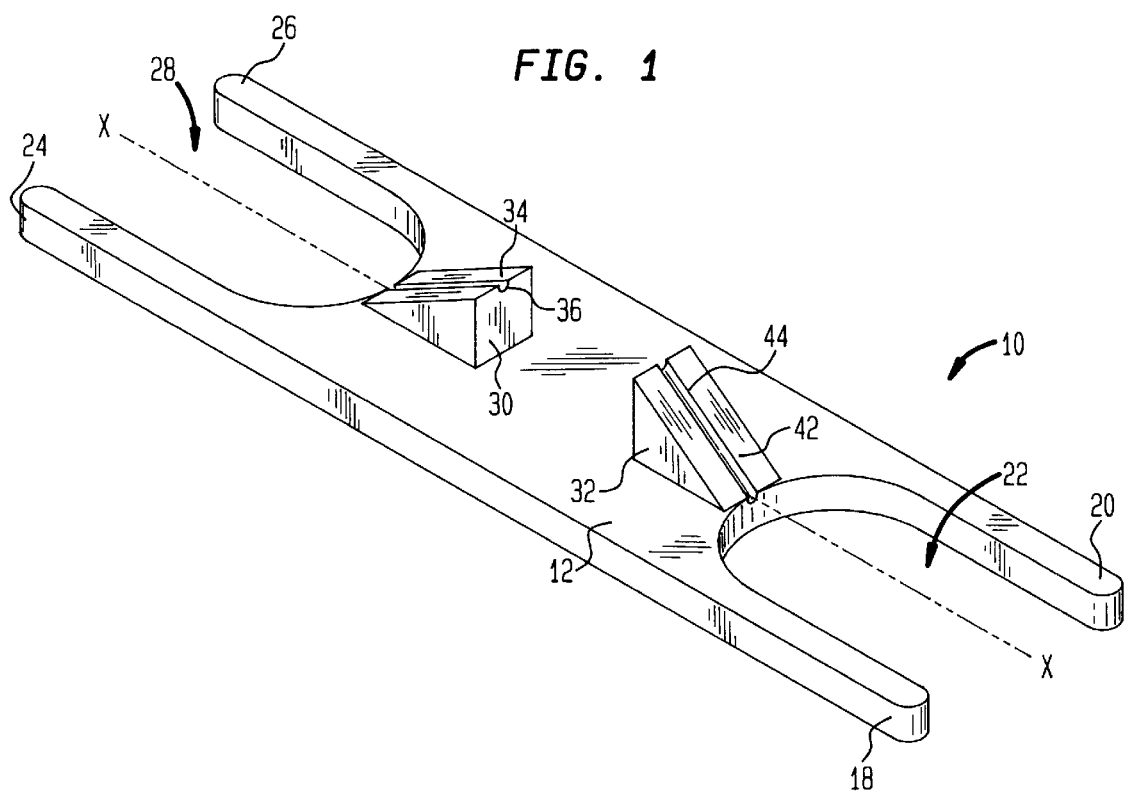
FIG. 1 is a perspective view of the needle guide of the present invention.
Figure 2:
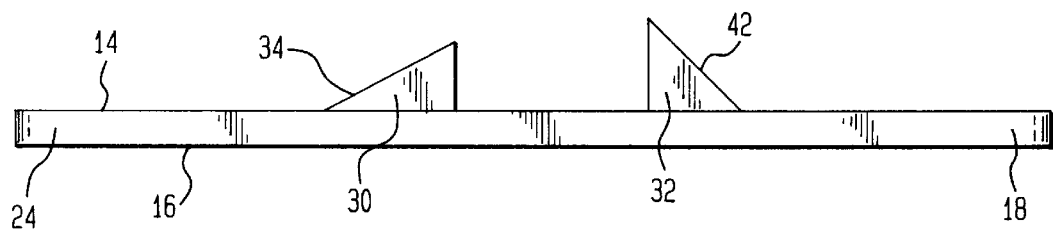
FIG. 2 is a side elevational view of the needle guide of FIG. 1.
Figure 3:
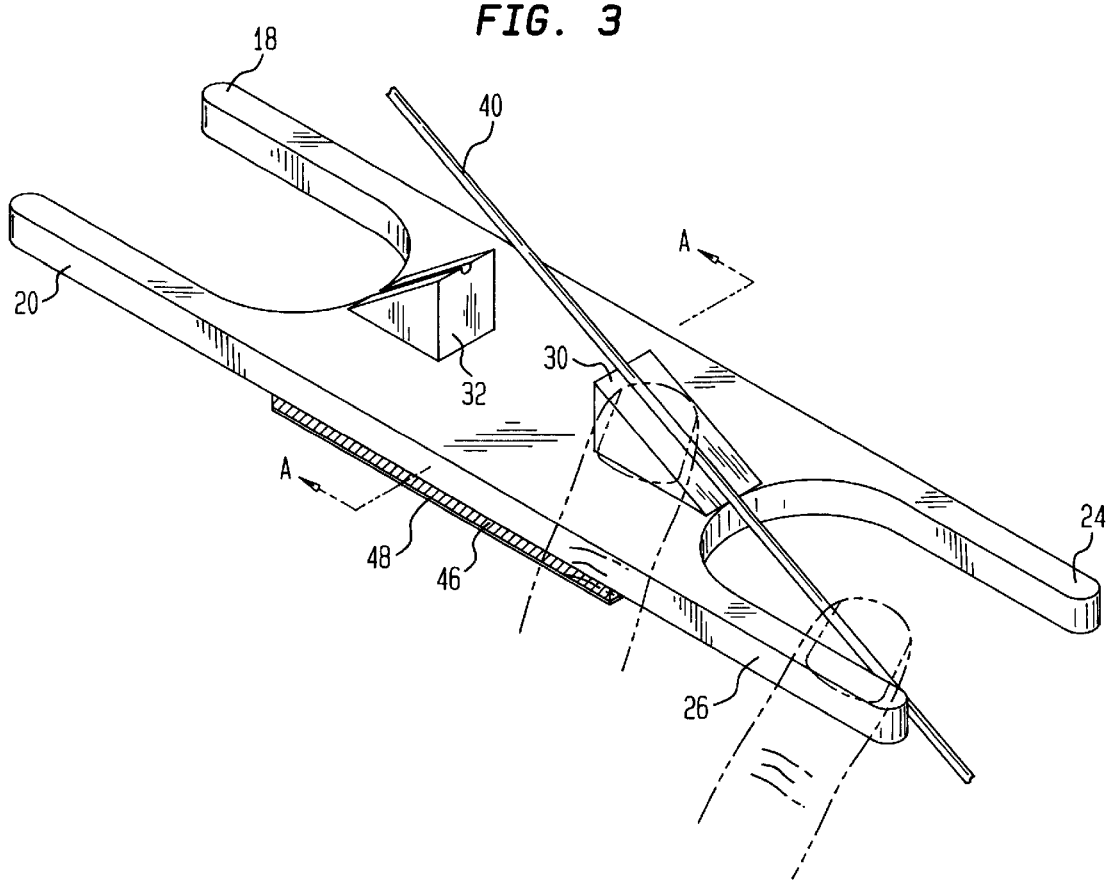
FIG. 3 is a perspective view showing the needle guide with a needle in the use position.
Figure 4:
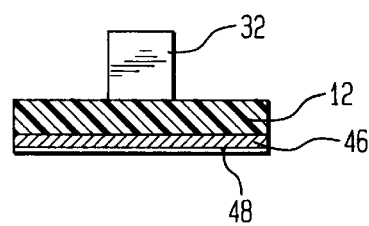
FIG. 4 is a cross-sectional view of the needle guide taken along line A—A of FIG. 3.

Referring to the figures, there is illustrated therein a needle guide 10 in accordance with the present invention. Needle guide 10 includes a base 12 having a top surface 14 and a bottom surface 16 which defines a plane for locating needle guide 10 on a patient's leg. As shown in the figures, the bottom surface 16 of base 12 is substantially flat. For the purpose of the present invention, however, bottom surface 16 need not be flat, but may be any configuration which defines a locating plane and which enables needle guide 10 to be stable and secure when resting on a patient's leg. For example, bottom surface 16 may include a series of spaced ribs, a squat wall depending from its periphery, a series of at least three flat bosses depending therefrom at spaced distances from one another or the like.

A pair of fingers 18 and 20 may project from one end of base 12 at a spaced distance from one another to define a recess or void space 22 therebetween. A similar pair of fingers 24 and 26 may project from the opposite end of base 12 at a spaced distance from one another to define a recess or void space 28 therebetween. Fingers 24 and 26 preferably extend parallel to fingers 18 and 20 so as to provide base 12 with an overall length in the direction of axis X—X which is greater than the width of base 12 in the direction perpendicular to axis X—X. As an example of its size, base 12 may have a length of about 4 inches and a width of about 1 inch, although base 12 may have dimensions which are larger, smaller or of a different proportion than these dimensions. As will be appreciated from the discussion below on the use of needle guide 10, fingers 24 and 26 may have a length which is less than the length of fingers 18 and 20.

On its top surface 14, base 12 preferably includes a pair of support members 30 and 32. Support member 30 has a support surface 34 which is oriented in a generally perpendicular direction to a vertical plane through axis X—X, and which is inclined relative to the locating plane of base 12 so as to define an angle of between about 20° and about 40° therebetween. An angle of about 30° between support surface 34 and the locating plane of base 12 is most preferred. Support surface 34 may include a channel 36 sized and shaped to cradle an angiographic needle 40 and to support the needle at the desired angle relative to the surface of the patient's skin. Channel 36 may be aligned in a vertical plane with axis X—X so that a needle 40 cradled in channel 36 will be aligned with the elongation direction of base 12.

Support member 32 is similar in construction to support member 30, and includes a support surface 42 which is oriented in a generally perpendicular direction to a vertical plane through axis X—X. However, support surface 42 is inclined at a different angle than support surface 34 relative to the locating plane of base 12. Thus, support surface 42 preferably is inclined so that the angle between surface 42 and the locating plane of base 12 is between about 40° and about 60°, with an angle of about 45° being most preferred. Surface 42 may include a channel 44 which is sized and shaped for supporting angiographic needle 40 at the desired angle relative to the surface of the patient's skin. Channel 44 may be aligned in a vertical plane with axis X—X so that when needle 40 is cradled therein, it will be aligned with the elongation direction of base 12. Although channel 44 is illustrated in the figures to be in alignment with the same vertical plane as channel 36, that is not necessarily the case. Thus, channels 36 and 44, and indeed support members 30 and 32, may be displaced from the central axis X—X of base 12. However, channels 36 and 44 preferably lie in vertical planes which are parallel to one another and to the vertical plane through axis X—X.

Needle guide 10 may optionally include an adhesive backing 46 on at least portions of the bottom surface 16 of base 12. The adhesive layer may include a protective sheet 48 such that removal of the protective sheet exposes the adhesive backing for attachment of needle guide 10 to a patient.

Figure 5:
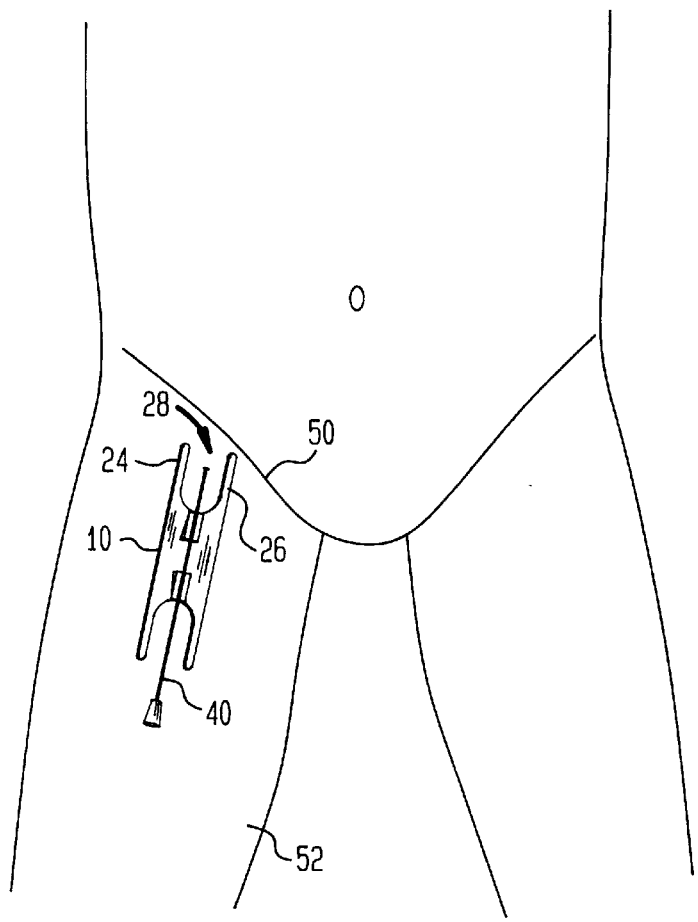
FIG. 5 is a highly schematic plan view showing the use position of the needle guide on a patient's leg.
Figure 6:
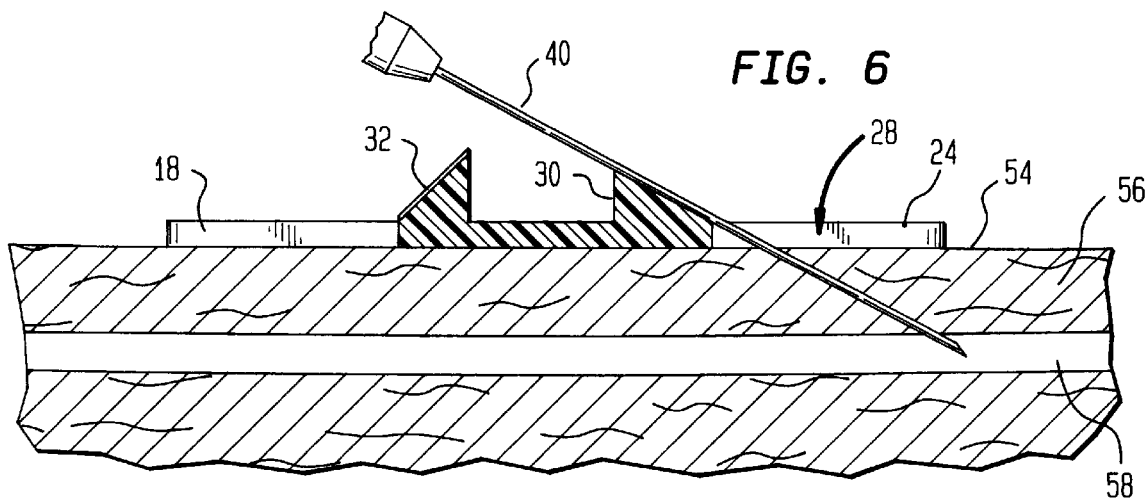
FIG. 6 is a highly schematic cross-sectional view showing the needle guide with a needle fully inserted in the patient's femoral artery.

The method for using needle guide 10 to insert angiographic needle 40 into the femoral artery of a patient of average weight will now be described with reference to FIGS. 5 and 6. In the first step of the procedure, the physician manually locates the femoral artery pulse at a point about 2 cm below the patient's inguinal crease 50. Needle guide 10 is then positioned so that the physician's pulse-finding finger lies within recess 22 with the ends of fingers 18 and 20 located at or below crease 50. With fingers 18 and 20 of sufficient length, this position assures that a needle guided by support member 30 will penetrate the patient's femoral artery 58 below crease 50. This position is important because it enables direct pressure to be applied to the femoral artery to stop bleeding once the percutaneous procedure has been completed. Should the needle penetrate the patient's femoral artery in the abdominal cavity, it would not be possible to apply direct pressure on the artery with the result that surgical intervention would be required to stop the arterial bleeding.

In any event, needle guide 10 also should be positioned so that the elongation axis X—X of base 12 is oriented in approximate alignment with the longitudinal axis of the patient's leg 52. Angiographic needle 40 is then placed on needle guide 10 so that it rests within channel 36 on support member 30, and is advanced through the patient's skin 54, subcutaneous tissue 56 and into the femoral artery 58. When the needle has entered the femoral artery 58, a spurt of arterial blood will exit the hub of needle 40. At this point, needle guide 10 may be moved down the patient's leg and away from needle 40 and the puncture site without the physician having to move his or her pulse-finding finger from the point of entry of the needle. After such use, needle guide 10 may be discarded.

The same procedure as described above would be used to insert an angiographic needle 40 into the femoral artery of an obese patient. In this case, however, needle guide 10 would be oriented in the opposite direction so that the physician's pulse-finding finger resides within recess 28 and the ends of fingers 24 and 26 are located at or below crease 50. Needle 40 would then be positioned in and guided by channel 44 in support member 32, and hence would enter the femoral artery at a more steep angle than that resulting from the use of support member 30 as described above. Because of the greater steepness of this entry angle, the distance between support member 32 and the point at which needle 40 enters the patient's skin would be less than the distance between the entry point and the support member when support member 30 is used. For that reason, as noted previously, fingers 24 and 26 may be shorter in length than fingers 18 and 20, yet would still properly position the needle so that it does not enter the patient's femoral artery within the patient's abdominal cavity.

It will be appreciated that needle guide 10 may be formed so as to have only a single support member thereon. Thus, one needle guide may be formed with a support member 30 having a support surface 34 which is inclined at an angle of between about 20° and 40°, and preferably at an angle of about 30°, relative to the locating plane of base 12. Another needle guide may include a support member 32 having a support surface 42 inclined at an angle of between about 40° and 60°, and preferably at an angle of about 45°, relative to the locating plane of base 12. Other needle guides may be provided with support surfaces oriented at still different angles. In such event, a needle guide would be selected for inserting a needle at the specific angle desired.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as set forth in the appended claims.

We claim:

1. A needle guide, comprising a base extending in an axial direction and having a surface defining an orientation plane;

a support member on said base defining a needle guide path inclined at an angle relative to said orientation plane, said needle guide path intersecting said orientation plane at a distance in said axial direction from a reference point on said base;

a locator on said base at a selected distance in said axial direction from said reference point, said selected distance being related to said angle and greater than said distance; and a recess extending in said axial direction through said base and having an open end, whereby said base may be moved in said axial direction from a first position with a needle positioned in said needle guide path so as to extend through said recess to a second position with the needle not extending through said recess and not positioned in said needle guide path.

2. The needle guide as claimed in claim 1, wherein said angle is between about 20° and about 40°.

3. The needle guide as claimed in claim 2, wherein said angle is about 30°.

4. The needle guide as claimed in claim 1, where said angle is between about 40° and 60°.

5. The needle guide as claimed in claim 4, wherein said angle is about 45°.

6. The needle guide as claimed in claim 1, wherein said base has a dimension in said axial direction which is greater than its dimension in a direction perpendicular to said axial direction.

7. The needle guide as claimed in claim 1, wherein said locator includes a pair of fingers projecting from said base and having free ends at said selected distance in said axial direction from said reference point, said pair of fingers being spaced apart from one another to define a recess therebetween.

8. The needle guide as claimed in claim 1, wherein said needle guide path lies in a plane oriented substantially parallel to said axial direction and substantially perpendicular to said orientation plane.

9. A needle guide, comprising a base extending in an axial direction and having a surface defining an orientation plane;

a first support member on said base defining a first needle guide path inclined at a first angle relative to said orientation plane, said first needle guide path intersecting said orientation plane at a first distance in said axial direction from a reference point on said base;

a first locator on said base at a selected distance in said axial direction from said reference point, said selected distance being related to said first angle and greater than said first distance;

a second support member on said base defining a second needle guide path inclined at a second angle relative to said orientation plane, said second needle guide path intersecting said orientation plane at a second distance in said axial direction from said reference point; and a second locator on said base at a predetermined distance in said axial direction from said reference point, said predetermined distance being related to said second angle and greater than said second distance.

10. The needle guide as claimed in claim 9, wherein said second angle is different from said first angle.

11. The needle guide as claimed in claim 10, wherein said first angle is between about 20° and about 40° and said second angle is between about 40° and about 60°.

12. The needle guide as claimed in claim 11, wherein said first angle is about 30°.

13. The needle guide as claimed in claim 12, wherein said second angle is about 45°.

14. The needle guide as claimed in claim 9, wherein said first locator includes a pair of fingers projecting from said base and having free ends at said selected distance in said axial direction from said reference point, said pair of fingers being spaced apart from one another to define a recess therebetween.

15. The needle guide as claimed in claim 14, wherein said second locator includes a pair of fingers projecting from said base and having free ends at said predetermined distance in said axial direction from said reference point, said pair of fingers being spaced apart from one another to define a recess therebetween.

16. The needle guide as claimed in claim 15, wherein said first pair of fingers have a length in said axial direction, and said second pair of fingers have a length in said axial direction which is less than said length of said first pair of fingers.

17. The needle guide as claimed in claim 9, wherein said base has a dimension in said axial direction which is greater than its dimension in a direction perpendicular to said axial direction.

18. The needle guide as claimed in claim 9, wherein said first and second needle guide paths lie in a plane oriented substantially parallel to said axial direction and substantially perpendicular to said orientation plane.

19. The needle guide as claimed in claim 9, wherein said first and second support members are oriented in opposite axial directions.

20. The needle guide as claimed in claim 9, wherein said predetermined distance is different from said selected distance.

* * * * *

UNITED STATES PATENT AND TRADEMARK OFFICE
CERTIFICATE OF CORRECTION

PATENT NO. : 5,911,707
DATED : June 15, 1999
INVENTOR(S) : Wolvek et al.

It is certified that error appears in the above-identified patent and that said Letters Patent is hereby corrected as shown below:

Column 2, line 9, delete "orientation".

Signed and Sealed this

Thirtieth Day of November, 1999

Attest:

Q. TODD DICKINSON

*Attesting Officer*  *Acting Commissioner of Patents and Trademarks*